(12) United States Patent
Candau

(10) Patent No.: US 7,416,721 B2
(45) Date of Patent: *Aug. 26, 2008

(54) SUNSCREEN COMPOSITIONS COMPRISING INSOLUBLE ORGANIC UV-SCREENING AGENTS AND HYDROXYALKYLUREA COMPOUNDS

(75) Inventor: Didier Candau, Bievres (FR)

(73) Assignee: L'Oreal, Paris (FR)

( * ) Notice: Subject to any disclaimer, the term of this patent is extended or adjusted under 35 U.S.C. 154(b) by 232 days.

This patent is subject to a terminal disclaimer.

(21) Appl. No.: 11/311,450

(22) Filed: Dec. 20, 2005

(65) Prior Publication Data

US 2006/0177394 A1   Aug. 10, 2006

Related U.S. Application Data

(60) Provisional application No. 60/646,599, filed on Jan. 26, 2005.

(30) Foreign Application Priority Data

Dec. 20, 2004   (FR) .................................. 04 53077

(51) Int. Cl.
*A61Q 17/04* (2006.01)
*A61Q 17/00* (2006.01)
*A61Q 19/04* (2006.01)
*A61Q 19/00* (2006.01)
*A61K 8/02* (2006.01)

(52) U.S. Cl. ........................... 424/59; 424/60; 424/400; 424/401

(58) Field of Classification Search ................... 424/59, 424/60, 400, 401
See application file for complete search history.

(56) References Cited

U.S. PATENT DOCUMENTS 5,980,872 A   11/1999   Luther et al.

FOREIGN PATENT DOCUMENTS

| DE | 2703185 A1 | 8/1978 |
|----|------------|--------|
| EP | 0893119 | 1/1999 |
| EP | 1 535 607 A1 | 6/2005 |

OTHER PUBLICATIONS

French Search Report corresponding to FR 04/53077, issued on Aug. 4, 2005, 1 page.

*Primary Examiner*—Shelley A. Dodson
(74) *Attorney, Agent, or Firm*—Buchanan, Ingersoll & Rooney, PC

(57) ABSTRACT

Cosmetic, notably anti-sun/sunscreen compositions having improved comfort after application onto keratin materials, e.g., human skin, contain at least one system for screening out UV radiation, and also contain:
(a) at least one insoluble organic UV-screening agent, and
(b) at least one hydroxyalkylurea compound of formula (I):

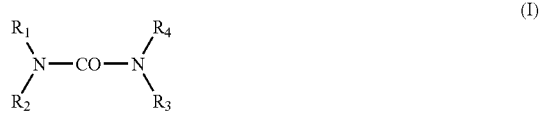

(I)

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate or isomer thereof, formulated into (c) a topically applicable, cosmetically acceptable carrier therefor.

24 Claims, No Drawings

SUNSCREEN COMPOSITIONS COMPRISING INSOLUBLE ORGANIC UV-SCREENING AGENTS AND HYDROXYALKYLUREA COMPOUNDS

CROSS-REFERENCE TO PRIORITY/PROVISIONAL APPLICATIONS

This application claims priority under 35 U.S.C. § 119 of FR 04/53077, filed Dec. 20, 2004, and of provisional application Ser. No. 60/646,599, filed Jan. 26, 2005, each hereby expressly incorporated by reference and each assigned to the assignee hereof.

CROSS-REFERENCE TO COMPANION APPLICATIONS

Copending applications Nos. 11/311,451, 11/311,650, 11/311,488, and 11/311,691, each filed concurrently herewith, each hereby expressly incorporated by reference and each assigned to the assignee hereof.

BACKGROUND OF THE INVENTION

1. Technical Field of the Invention

The present invention relates to sunscreen compositions comprising, formulated into a cosmetically acceptable carrier, at least one system for screening out UV radiation, and containing:

(a) at least one insoluble organic UV-screening agent,
(b) at least one specific hydroxyalkylurea compound.

This invention also relates to the formulation of a hydroxyalkylurea compound of specific formula into a composition in the form of an emulsion, comprising at least one water-soluble UV-screening agent, for improving the comfort after application, in particular the softness to the touch.

2. Description of Background and/or Related and/or Prior Art

It is well known that light radiation with wavelength of from 280 nm to 400 nm permits tanning of the human epidermis and that rays with wavelengths of from 280 to 320 nm, which are known as UV-B rays, cause skin burns and erythema that can harm the development of a natural tan; this UV-B radiation should therefore be screened out.

It is also known that UV-A rays, with wavelengths of from 320 to 400 nm, which cause tanning of the skin, are liable to induce an impairment in the skin, especially in the case of sensitive skin or skin that is continually exposed to solar radiation. UV-A rays in particular bring about a loss of elasticity of the skin and the appearance of wrinkles, leading to premature aging. They promote the triggering of the erythemal reaction or amplify this reaction in certain individuals and may even be the cause of phototoxic or photoallergic reactions. It is therefore desirable also to screen out UV-A radiation.

UV-A and UV-B rays should therefore be screened out, and cosmetic compositions for protecting the human epidermis containing UV-A- and UV-B-screening agents currently exist.

These anti-sun compositions are quite often in the form of an emulsion, of oil-in-water type (i.e., a cosmetically and/or dermatologically acceptable carrier consisting of a continuous aqueous dispersing phase and of a discontinuous fatty dispersed phase), or of water-in-oil type (aqueous phase dispersed in a continuous fatty phase), which contains, in varying concentrations, one or more conventional lipophilic organic screening agents and/or conventional hydrophilic organic screening agents capable of selectively absorbing the harmful UV radiation, these screening agents (and the amounts thereof) being selected as a function of the desired sun protection factor, the sun protection factor (SPF) being expressed mathematically as the ratio of the dose of UV radiation required to reach the erythema-forming threshold with the UV-screening agent to the dose of the UV radiation required to reach the erythema-forming threshold without the UV-screening agent. In such emulsions, the hydrophilic screening agents are present in the aqueous phase and the lipophilic screening agents are present in the fatty phase.

The UV-screening agents most commonly used are organic and soluble in oils or in aqueous media; they generally have, within their structure, a chromophore group linked to a solubilizing group, which is generally a fatty chain in the case of liposoluble UV-screening agents or else a carboxylic or sulfonic acid group in the case of water-soluble UV-screening agents.

The prior art describes micronized insoluble organic UV-screening agents with a mean particle size ranging from 10 nm to 2 µm, which have the advantage of being more effective than their soluble homologues comprising the same chromophore group to an equivalent degree. UV-screening agents of this type are in particular described in EP-746,305 and EP-8-405,395. However, certain anti-sun formulations containing this type of screening agent have a tendency, after application, to make the skin rough.

Another difficulty lies in the fact that anti-sun emulsions based on insoluble UV-screening agents, after application to the skin, produce an uneven, nonhomogeneous, or even coarse, distribution of the insoluble UV-screening agents on the skin, which may be harmful to the quality of the desired overall protective effect. This poor distribution that is observed at the surface of the skin is often linked to the fact that, in terms of the emulsion, there is a substantial lack of homogeneity after application.

SUMMARY OF THE INVENTION

After considerable research in the field of photoprotection, it has now unexpectedly and surprisingly been determined that, by adding, to an anti-sun/sunscreen composition containing at least one organic insoluble UV-screening agent, a hydroxyalkylurea of formula (1) more fully described hereinafter, it is possible to substantially improve the cosmetic properties such as the slipperiness or the softness to the touch, after application. The anti-sun/sunscreen compositions containing such a combination also exhibit good water remanence, perspiration remanence and washing remanence, and also good persistence over time.

This discovery forms the basis of the present invention.

Thus, the present invention features compositions comprising, formulated into a cosmetically acceptable carrier, at least one system for screening out UV radiation, and which comprises:

(a) at least one insoluble organic UV-screening agent, and
(b) at least one hydroxyalkylurea of formula (1) more fully described hereinafter.

The present invention also features the use of at least one hydroxyalkylurea of formula (1) in a composition comprising, in a cosmetically acceptable carrier, at least one insoluble organic UV-screening agent, for improving the comfort after application, in particular the softness to the touch.

In the remainder of the present description, the expression "system for screening out UV radiation" means an agent for screening out UV radiation, comprising either a single organic or inorganic compound for screening out UV radiation, or a mixture of several organic or inorganic compounds for screening out UV radiation, for example a mixture comprising a UV-A-screening agent and a UV-B-screening agent.

In the remainder of the present description, the expression "insoluble organic UV-screening agent" means, for the purpose of the present invention, an organic compound for screening out UV radiation that has a water-solubility of less than 0.1% by weight and a solubility of less than 1% by weight in most organic solvents, such as paraffin oil, fatty alcohol benzoates and fatty acid triglycerides.

Other characteristics, aspects and advantages of the invention will become apparent from the detailed description that will follow.

DETAILED DESCRIPTION OF BEST MODE AND SPECIFIC/PREFERRED EMBODIMENTS OF THE INVENTION

The hydroxyalkylureas in accordance with the invention are selected from among those corresponding to general formula (1):

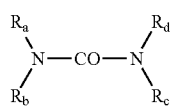

(1)

in which $R_a$, $R_b$, $R_c$ and $R_d$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_a$-$R_d$ representing a hydroxyalkyl group, and also the salts, solvates and isomers thereof.

In formula (1), among the alkyl groups, mention may in particular be made of methyl, ethyl, n-propyl, isopropyl, n-butyl, isobutyl and tert-butyl radicals.

The compounds of formula (1) that are preferred are those that contain only one hydroxyalkyl group, i.e., those for which $R_a$ is a hydroxyalkyl group and $R_b$, $R_c$ and $R_d$ represent, independently of one another, a hydrogen atom or a $C_1$-$C_4$ alkyl radical. The compounds of formula (1) for which $R_a$ is a hydroxyalkyl group and $R_b$, $R_c$ and $R_d$ each represent a hydrogen atom are more particularly preferred.

Among the hydroxyalkyl groups, preference is given to those containing a single hydroxyl group, and in particular hydroxyethyl, hydroxypropyl, hydroxybutyl, hydroxypentyl and hydroxyhexyl groups. The hydroxyethyl group is preferred.

As compounds of formula (1) that are preferred, mention may be made of N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(trishydroxymethylmethyl)urea; N-ethyl-N'-(2-hydroxyethyl)urea; N,N-bis-(2-hydroxyethyl)urea; N,N'-bis-(2-hydroxyethyl)urea; N,N-bis-(2-hydroxypropyl)urea; N,N'-bis-(2-hydroxypropyl)urea; N,N-bis-(2-hydroxyethyl)-N'-propylurea; N,N-bis-(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis-(2-hydroxyethyl)-N', N'-dimethylurea; N,N,N',N'-tetrakis-(2-hydroxyethyl)urea; and N',N'-bis-(2-hydroxyethyl)-N',N'-bis-(2-hydroxypropyl) urea.

A compound that is particularly preferred according to the present invention is N-(2-hydroxyethyl)urea, hereinafter referred to as "hydroxyethylurea".

The hydroxyalkylureas of formula (1) can be prepared as described in DE-2703185. Among these, hydroxyethylurea is also commercially available, in the form of a mixture at 50% by weight in water, from the company National Starch under the trademark Hydrovance®.

Among the salts, mention may be made of salts of inorganic acids, such as sulfuric acid, hydrochloric acid, hydrobromic acid, hydriodic acid, phosphoric acid or boric acid. Mention may also be made of the salts of organic acids, which may contain one or more carboxylic, sulfonic or phosphonic acid groups. They may be linear, branched or cyclic aliphatic acids or else aromatic acids. These acids may also contain one or more hetero atoms selected from O and N, for example in the form of hydroxyl groups. Mention may in particular be made of propionic acid, acetic acid, terephthalic acid, citric acid and tartaric acid.

The term "solvate" means a stoichiometric mixture of said compound of formula (1) with one or more molecules of water or of organic solvent, such a mixture being derived from the synthesis of the compound of formula (1).

The hydroxyalkylureas in accordance with the invention are preferably present in the compositions in accordance with the invention at contents of from 0.01 to 50% by weight, and more preferably from 0.1 to 20%, and even more preferably from 0.1 to 10% by weight relative to the total weight of the composition.

The insoluble organic UV-screening agents containing at least one group for absorbing UV radiation can be selected in particular from insoluble organic UV-screening agents of oxalanilide, triazine, benzotriazole, vinylamide, cinnamide, benzazole, benzofuran, arylvinylidene ketone, acrylonitrile amide, acrylonitrile sulfonamide, acrylonitrile carbamate or phenylenebisbenzoxazinone type.

Among insoluble UV-screening agents of oxalanilide type, mention may be made of those corresponding to the formula:

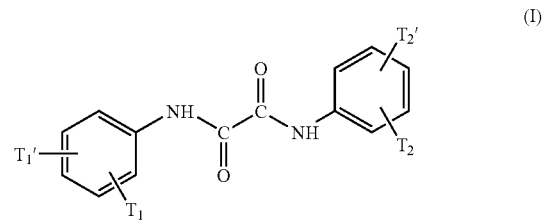

(I)

in which $T_1$, $T_1'$, $T_2$ and $T_2'$ each independently represent a $C_1$-$C_8$ alkyl radical or a $C_1$-$C_8$ alkoxy radical. These compounds are described in WO 95/22959. By way of examples, mention may be made of the commercial products Tinuvin® 315 and Tinuvine 312 marketed by Ciba-Geigy corresponding, respectively, to the formulae:

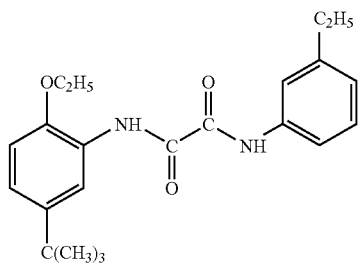

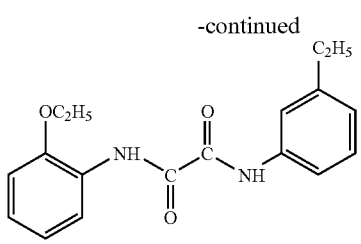

The insoluble screening agents of triazine type correspond to the general formula below:

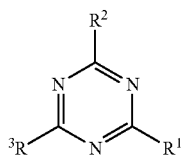

(II)

in which $R^1$, $R^2$ and $R^3$ each independently represent a phenyl, phenoxy or pyrrolo group that is unsubstituted or that bears, each independently, one, two or three substituents selected from among —OH, $C_1$-$C_{18}$ alkyl, $C_1$-$C_{18}$ alkoxy, carboxy($C_1$-$C_{18}$)alkyl, $C_5$-$C_8$ cycloalkyl, methylbenzylidenecamphor, and —(CH=CR')$_n$(CO)—OR$^4$ where R' represents a hydrogen atom, a cyano group or a COOR$^4$ group, with $R^4$=$C_1$-$C_{18}$ alkyl or cinnamyl, and n is 0 or 1.

These compounds are described in WO 97/03643, GB-2286774, EP-743,309, WO 98/22447, GB-2319523 and EP-A-0-790,243.

Mention will be made, more particularly, of the following compounds:
2,4,6-tris(diethyl 4'-aminobenzalmalonate)-s-triazine,
2,4,6-tris(diisopropyl 4'-aminobenzalmalonate)-s-triazine,
2,4,6-tris(dimethyl 4'-aminobenzalmalonate)-s-triazine,
2,4,6-tris(ethyl α-cyano-4-aminocinnamate)-s-triazine.

Among the UV-screening agents of triazine type that can be used for the present invention, mention may also be made of insoluble derivatives of s-triazine bearing benzotriazole and/or benzothiazole groups, such as those described in WO 98/25922.

Among these compounds, mention may more particularly be made of 2,4,6-tris[(3'-benzotriazol-2-yl-2'-hydroxy-5'-methyl)phenylamino]-s-triazine and 2,4,6-tris[(3'-benzotriazol-2-yl-2'-hydroxy-5'-tert-octyl)phenylamino]-s-triazine.

Among the insoluble organic UV-screening agents of benzotriazole type, mention may be made of those of formula (III) below, described, for example, in WO 95/22959:

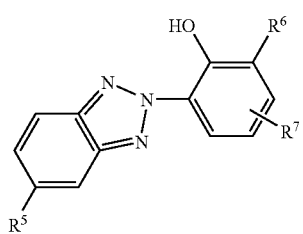

(III)

in which $R^5$ denotes a hydrogen atom or a $C_1$-$C_{18}$ alkyl radical, and $R^6$ and $R^7$, which may be identical or different, each independently denote a $C_1$-$C_{18}$ alkyl radical optionally substituted with a phenyl group.

By way of examples of compounds of formula (III), mention may be made of the commercial products Tinuvin® 328, 320, 234 and 350 from the company Ciba-Geigy corresponding, respectively, to the formulae below:

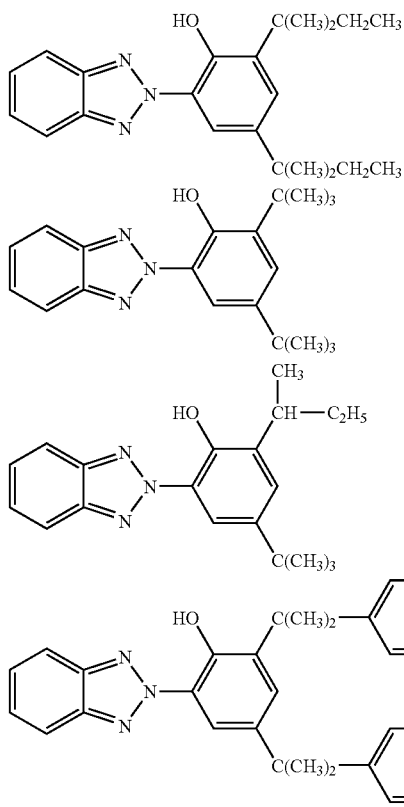

Among the insoluble organic UV-screening agents of benzotriazole type, mention may also be made of the compounds described in U.S. Pat. Nos. 5,687,521, 5,373,037 and 5,362,881, and, among these, in particular [2,4'-dihydroxy-3-(2H-benzotriazol-2-yl)-5-(1,1,3,3-tetramethylbutyl)-2'-n-octoxy-5'-benzoyl]diphenylmethane of formula:

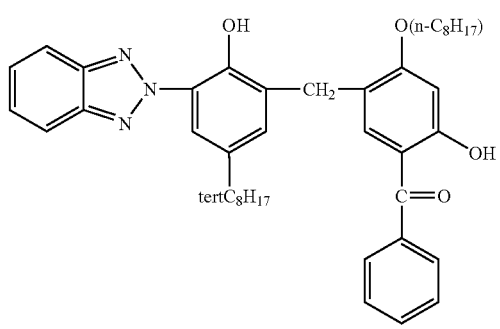

marketed under the name Mixxim® PB30 by Fairmount Chemical.

Other insoluble organic UV-screening agents of benzotriazole type are the methylenebis(hydroxyphenylbenzotriazole) derivatives having the structure below:

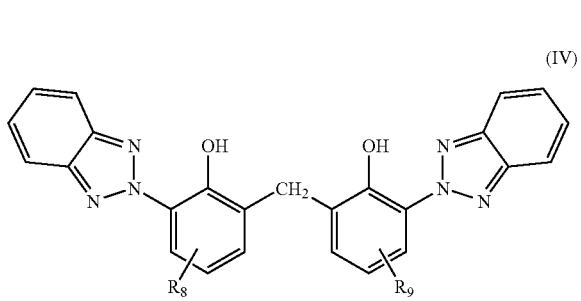

(IV)

in which $R^8$ and $R^9$, which may be identical or different, each represent a $C_1$-$C_{18}$ alkyl radical that may be substituted with one or more radicals selected from $C_1$-$C_4$ alkyl, $C_5$-$C_{12}$ cycloalkyl, or aryl. These compounds are known and are described in U.S. Pat. Nos. 5,237,071, 5,166,355, GB-A-2303549, DE-19726184 and EP-A-893,119.

In formula (IV) defined above, the $C_1$-$C_{18}$ alkyl radicals may be linear or branched and are, for example, methyl, ethyl, n-propyl, isopropyl, n-butyl, isobutyl, tert-butyl, tert-octyl, n-amyl, n-hexyl, n-heptyl, n-octyl, isooctyl, n-nonyl, n-decyl, n-undecyl, n-dodecyl, tetradecyl, hexyldecyl or octadecyl; the $C_5$-$C_{12}$ cycloalkyl radicals are, for example, cyclopentyl, cyclohexyl or cyclooctyl; the aryl radicals are, for example, phenyl or benzyl.

Among the compounds of formula (IV), those having the structures below are more particularly preferred:

compound (a)

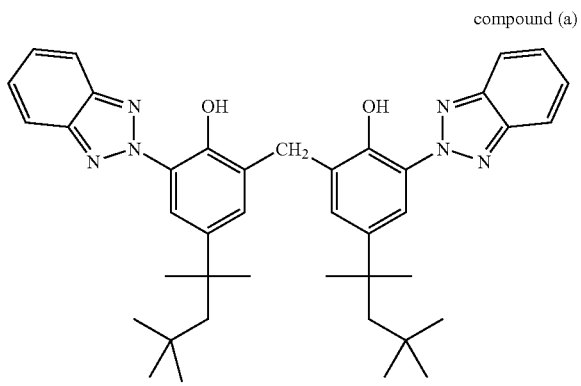

compound (b)

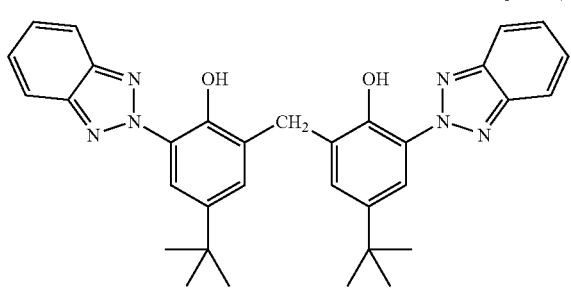

compound (c)

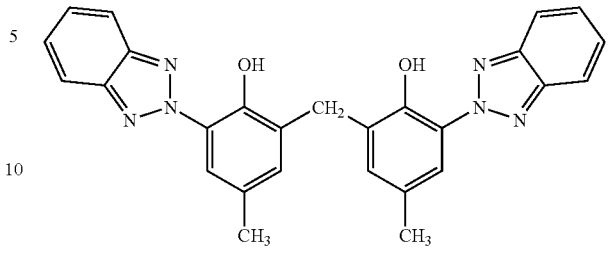

Compound (a) having the nomenclature 2,2'-methylenebis-[6-(2H-benzotriazol-2-yl)-4-(1,1,3,3-tetramethylbutyl)phenol] is marketed in solid form under the name Mixxim BB/100 by Fairmount Chemical and in micronized form under the name Tinosorb M by Ciba Specialty Chemicals.

Compound (c) having the nomenclature 2,2'-methylenebis-[6-(2H-benzotriazol-2-yl)-4-(methyl)phenol] is marketed in solid form under the name Mixxim BB/200 by Fairmount Chemical.

Among the insoluble organic screening agents of the vinylamide type, mention may, for example, be made of the compounds of formula (V) which are described in WO 95/22959:

$$T_3\text{-}(Y)_r\text{---}C(=\!O)\text{---}C(T_4)=\!C(T_5)\text{---}N(T_6)(T_7) \quad (V)$$

in which $T_3$ is a $C_1$-$C_{18}$, preferably $C_1$-$C_5$, alkyl radical or a phenyl group optionally substituted with one, two or three radicals selected from among OH, $C_1$-$C_{18}$ alkyl, $C_1$-$C_8$ alkoxy or —C(=O)—OT$_8$ wherein $T_8$ represents a $C_1$-$C_{18}$ alkyl radical; $T_4$, $T_5$, $T_6$ and $T_7$ each independently represent a $C_1$-$C_{18}$, preferably $C_1$-$C_5$, alkyl radical or a hydrogen atom; Y represents an —NH-group or an oxygen atom and r is 0 or 1.

Among these compounds, mention may more particularly be made of:
4-octylamino-3-penten-2-one;
ethyl 3-octylamino-2-butenoate;
3-octylamino-1-phenyl-2-buten-1-one;
3-dodecylamino-1-phenyl-2-buten-1-one.

Among the organic screening agents of cinnamide type, mention may be made of the compounds such as those described in WO 95/22959 and corresponding to the formula below:

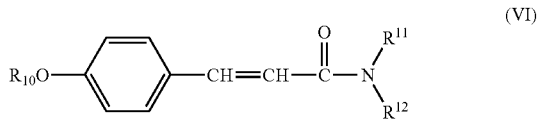

(VI)

in which:

$R_{10}$ represents a hydrogen atom or a $C_1$-$C_4$ alkyl radical, preferably methyl or ethyl, $R^{11}$ represents a hydrogen atom or a $C_1$-$C_4$ alkyl radical, preferably methyl or ethyl, $R^{12}$ represents a —(CONH)$_s$-phenyl radical wherein s is 0 or 1 and the phenyl group may be substituted with one, two or three groups selected from OH, $C_1$-$C_{18}$ alkyl, $C_1$-$C_8$ alkoxy or —C(=O)—OR$^{13}$ where R$^{13}$ is a-$C_1$-$C_{18}$ alkyl, and more preferably R$^{12}$ represents a phenyl, 4-methoxyphenyl or phenylaminocarbonyl radical.

Mention may also be made of the bis[α,β-disubstituted cinnamide] dimers described, for example, in U.S. Pat. No. 5,888,481, having the structure:

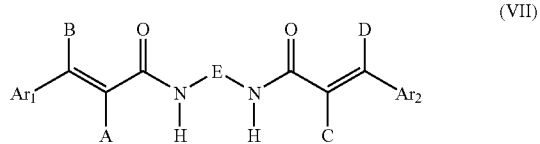

(VII)

in which:
- Ar1 and Ar2, which may be identical or different, each represent a phenyl radical, an aromatic heterocycle, a group comprising a condensed phenyl ring or a group comprising a condensed aromatic heterocycle, and may bear one or more substituents, which may be identical or different,
- B and D, which are other than a hydrogen atom, each independently represent an organic radical,
- A and C each independently represent an organic radical, and
- E represents a divalent organic radical,
- with the exclusion of the compounds for which Ar1 and Ar2 both represent a phenyl group bearing a substituent —OR where R represents a hydrogen atom or an organic radical, A and C both represent a cyano group, B and D both represent a $C_1$-$C_{35}$ alkyl or alkenyl group, and E represents a divalent organic radical,
- and in particular the compound having the structure:

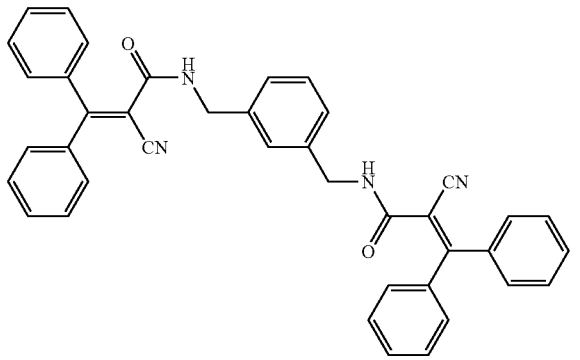

Among the insoluble organic screening agents of the benzazole type, mention may be made of those corresponding to one of the formulae below:

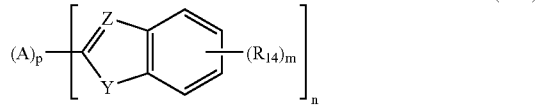

(VIII)

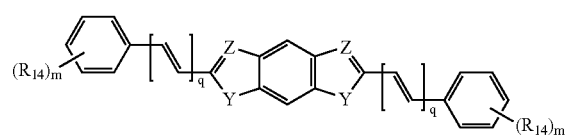

(IX)

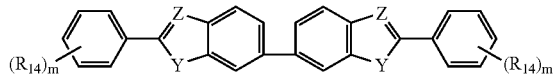

(X)

in which:
- each of the symbols Y independently represents an oxygen or sulfur atom or an NR$_{15}$ group,
- each of the symbols Z independently represents a nitrogen atom or a CH group,
- each of the symbols R$_{14}$ independently represents an OH group, a halogen atom, a linear or branched $C_1$-$C_8$ alkyl radical optionally containing a silicon atom, or a linear or branched $C_1$-$C_8$ alkoxy group,
- each of the numbers m is independently 0, 1 or 2,
- n represents an integer between 1 and 4 inclusive,
- p is equal to 0 or 1,
- each of the numbers q is independently equal to 0 or 1,
- each of the symbols R$_{15}$ independently represents a hydrogen atom, a benzyl group, or a linear or branched $C_1$-$C_8$ alkyl radical optionally containing a silicon atom, A represents a radical having a valency n, selected from those of formulae:

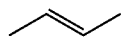

(a)

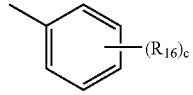

(b)

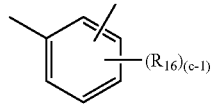

(c)

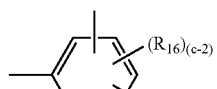

(d)

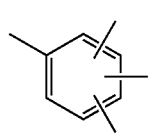

(e)

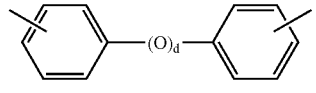

(f)

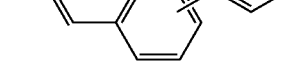

(g)

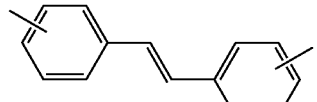

(h)

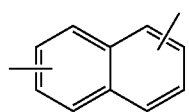

(i)

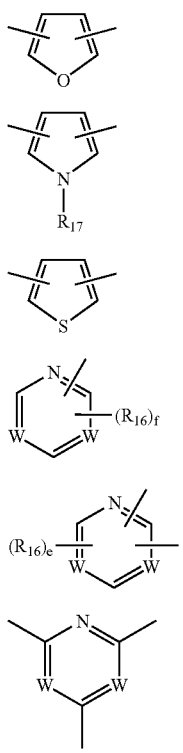

(j)

(k)

(l)

(m)

(n)

(o)

in which each of the symbols $R_{16}$ independently represents a halogen atom, or a linear or branched $C_1$-$C_4$ alkyl or alkoxy radical or a hydroxyl radical, $R_{17}$ represents a hydrogen atom or a linear or branched $C_1$-$C_4$ alkyl radical, c=0-4, d=0-3, e=0 or 1 and f=0-2.

These compounds are in particular described in DE-676 103 and CH-350763, U.S. Pat. Nos. 5,501,850, 5,961,960, EP-O-669,323, U.S. Pat. Nos. 5,518,713, 2,463,264, the article from J. Am. Chem. Soc., 79, 5706-5708,1957, the article published in J. Am. Chem. Soc., 82, 609-611,1960, EP-O-921,126 and EP-O-712,855.

By way of examples of preferred compounds of formula (VIII) of the 2-arylbenzazole family, mention may be made of 2-benzoxazol-2-yl-4-methylphenol, 2-(1H-benzimidazol-2-yl)-4-methoxyphenol or 2-benzothiazol-2-ylphenol, it being possible for these compounds to be prepared, for example, according to the processes described in CH-350763.

By way of examples of preferred compounds of formula (VIII) of the benzimidazolylbenzazole family, mention will be made of 2,2'-bisbenzimidazole, 5,5',6,6'-tetramethyl-2,2'-bisbenzimidazole, 5,5'-dimethyl-2,2'-bisbenzimidazole, 6-methoxy-2,2'-bisbenzimidazole, 2-(1H-benzimidazol-2-yl)benzothiazole, 2-(1H-benzimidazol-2-yl)benzoxazole and N,N'-dimethyl-2,2'-bisbenzimidazole, it being possible for these compounds to be prepared according to the procedures described in U.S. Pat. Nos. 5,961,960 and 2,463,264.

By way of examples of preferred compounds of formula (VIII) of the phenylenebenzazole family, mention will be made of 1,4-phenylenebis-(2-benzoxazolyl), 1,4-phenylenebis-(2-benzimidazolyl), 1,3-phenylenebis-(2-benzoxazolyl), 1,2-phenylenebis-(2-benzoxazolyl), 1,2-phenylenebis(benzimidazolyl), 1,4-phenylenebis-(N-2-ethylhexyl-2-benzimidazolyl) and 1,4-phenylenebis-(N-trimethylsilylmethyl-2-benzimidazolyl), it being possible for these compounds to be prepared according to the procedures described in U.S. Pat. No. 2,463,264 and in the publications J. Am. Chem. Soc., 82, 609 (1960) and J. Am. Chem. Soc., 79, 5706-5708 (1957).

By way of examples of preferred compounds of formula (VIII) of the benzofuranylbenzoxazole family, mention will be made of 2-(2-benzofuranyl)benzoxazole, 2-(benzofuranyl)-5-methylbenzoxazole and 2-(3-methyl-2-benzofuranyl) benzoxazole, it being possible for these compounds to be prepared according to the procedures described in U.S. Pat. No. 5,518,713.

As preferred compounds of formula (IX), mention may, for example, be made of 2,6-diphenyl-1,7-dihydrobenzo[1,2-d; 4,5-d']diimidazole corresponding to the formula:

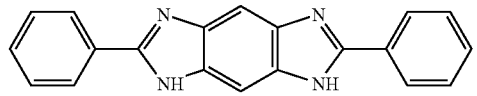

or 2,6-distyryl-1,7-dihydrobenzo[1,2-d;4,5-d']diimidazole or else 2,6-di-(p-tert-butylstyryl)-1,7-dihydrobenzo[1,2-d;4, 5-d']diimidazole, which may be prepared according to the processes described in EP-O-669,323.

As a preferred compound of formula (X), mention may be made of 5,5'-bis[(phenyl-2-)benzimidazole] having the formula:

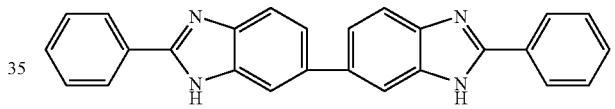

the preparation of which is described in J. Chim. Phys., 64,1602 (1967).

Among these insoluble organic compounds for screening out UV radiation, 2-(1H-benzimidazol-2-yl)benzoxazole, 6-methoxy-2,2'-bisbenzimidazole, 2-(1H-benzimidazol-2-yl)benzothiazole, 1,4-phenylenebis-(2-benzoxazolyl), 1,4-phenylenebis-(2-benzimidazolyl), 1,3-phenylenebis-(2-benzoxazolyl), 1,2-phenylenebis-(2-benzoxazolyl), 1,2-phenylenebis-(2-benzimidazolyl) and 1,4-phenylenebis-(N-trimethylsilylmethyl-2-benzimidazolyl) are most particularly preferred.

Another family of insoluble screening agents is that of the arylvinylene ketones, selected from those corresponding to one of the formulae (XI) and (XII) below:

(XI)

(XII)

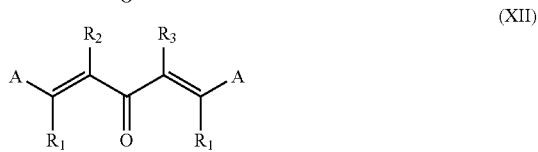

in which:
n=1 or 2,
A, in formula (XI) when n=1 or in formula (XII), is an aryl radical selected from formulae (a) to (d) below, or, in formula (XI) when n=2, is a radical selected from formulae (e) to (h) below:

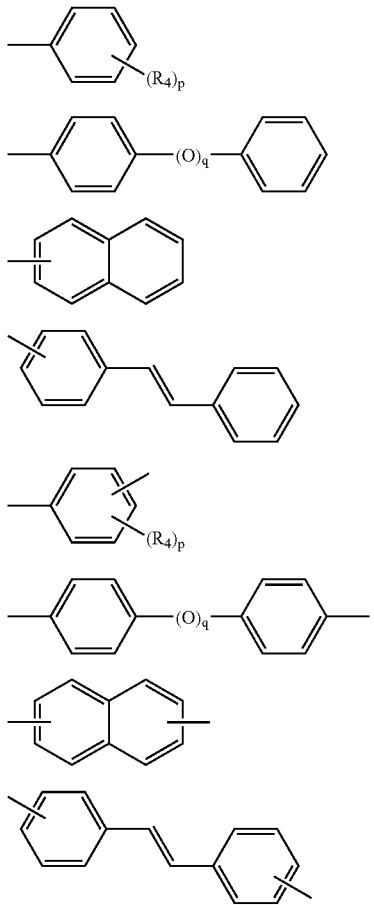

in which:
each of the symbols $R_4$ independently represents an OH group, a halogen atom, a linear or branched $C_1$-$C_6$ alkyl radical optionally containing a silicon atom, a linear or branched $C_1$-$C_6$ alkoxy radical optionally containing a silicon atom, a linear or branched $C_1$-$C_5$ alkoxycarbonyl radical, or a linear or branched $C_1$-$C_6$ alkylsulfonamide radical optionally containing a silicon atom or an amino acid function,
p represents an integer between 0 and 4 inclusive,
q represents 0 or 1,
$R_1$ represents hydrogen or an OH group,
$R_2$ represents hydrogen, a linear or branched $C_1$-$C_6$ alkyl radical optionally containing a silicon atom, a cyano group, a $C_1$-$C_6$ alkylsulfonyl radical, or a phenylsulfonyl radical,
$R_3$ represents a linear or branched $C_1$-$C_6$ alkyl radical optionally containing a silicon atom or a phenyl group that can form a bicycle and that is optionally substituted with one or two radicals $R_4$,
or $R_2$ and $R_3$ together form a monocyclic, bicyclic or tricyclic $C_2$-$C_{10}$ hydrocarbon-based residue optionally interrupted with one or more nitrogen, sulfur and oxygen atoms and optionally containing another carbonyl, and optionally substituted with a linear or branched $C_1$-$C_8$ alkylsulfonamide radical optionally containing a silicon atom or an amino acid function; on the condition that, when n=1, $R_2$ and $R_3$ do not form a camphor ring.

By way of examples of insoluble compounds for screening out UV radiation, of formula (XI) in which n=1, mention may be made of the following families:

Styryl ketone (Kao JP-04,134,042) such as 1-(3,4-dimethoxyphenyl)-4,4-dimethylpent-1-en-3-one:

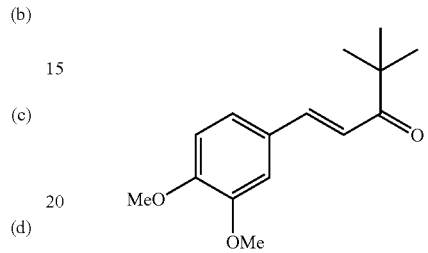

Benzylidene cineole (E. Mariani et al, 16$^{th}$ IFSCC Congress, New York (1990)) such as 1,3,3-trimethyl-5-(4-methoxybenzylidene)-2-oxabicyclo[2.2.2]octan-6-one:

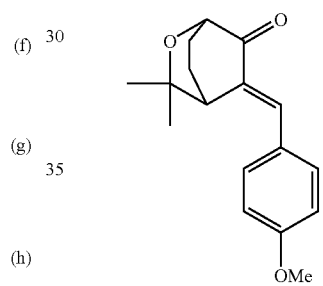

Benzylidene chromanone (Kao JP-04-134,043) such as 3-(4-methoxybenzylidene)-2,3,4a,8a-tetrahydrochromen-4-one:

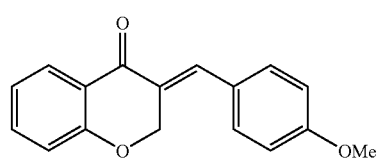

Benzylidene thiochromanone (Kao JP-04-134,043) such as 3-(4-methoxybenzylidene)-2,3,4a,8a-tetrahydrochromen-4-thione:

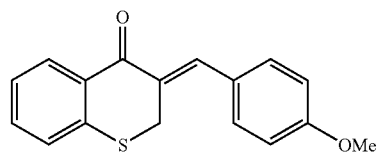

Benzylidene quinuclidinone (Merck EP-O-576,974) such as 4-methoxybenzylidene-1-azabicyclo[2.2.2]octan-3-one:

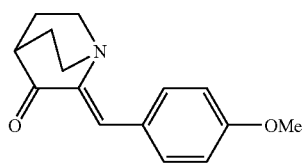

Benzylidene cycloalkanone (Henkel FR-2-395,023) such as 2-(4-methoxybenzylidene)cyclopentanone and 2-(4-methoxybenzylidene)cyclohexanone:

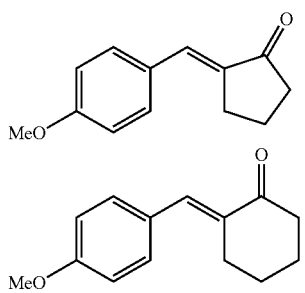

Benzylidene hydantoin (Ajinomoto JP-01-158,090) such as 5-(3,4-dimethoxybenzylidene)imidazolidine-2,4-dione:

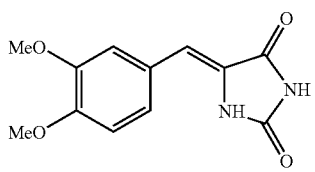

Benzylidene indanone (Kao JP-04-134,043) such as 2-(4-methoxybenzylidene)indan-1-one:

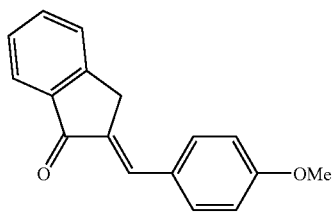

Benzylidene tetralone (Kao JP-04-134,043) such as 2-(4-methoxybenzylidene)-3,4-dihydro-2H-naphthalen-1-one:

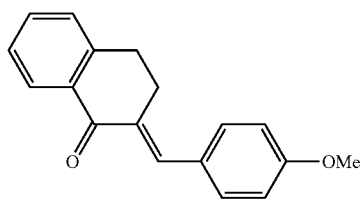

Benzylidene furanone (L'Oréal EP-O-390,683) such as 4-(4-methoxybenzylidene)-2,2,5,5-tetramethyldihydrofuran-3-one:

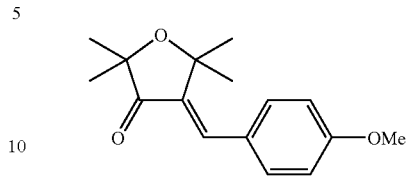

Benzylidene benzofuranone (Kao JP-04-134,041) such as 2-benzylidenebenzofuran-3-one:

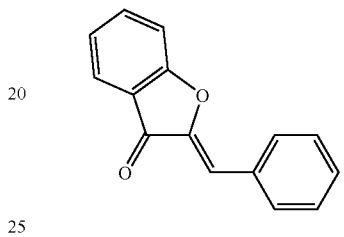

Benzylidene indanedione such as 2-(3,5-di-tert-butyl-4-hydroxybenzylidene)indan-1,3-dione:

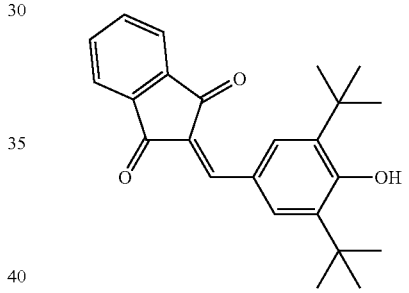

Benzylidene benzothiofuranone (Kao JP-04-134,043) such as 2-benzylidenebenzo[b]thiophen-3-one:

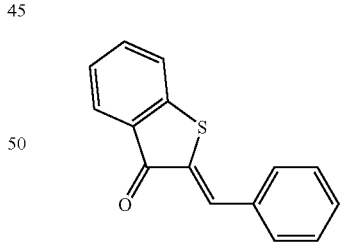

Benzylidene barbituric such as 5-(4-methoxybenzylidene)-1,3-dimethylpyrimidine-2,4,6-trione:

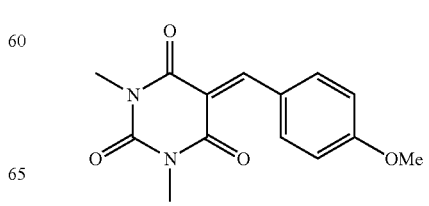

Benzylidene pyrazolone such as 4-(4-methoxyben-zylidene)-5-methyl-2-phenyl-2,4-dihydropyrazol-3-one:

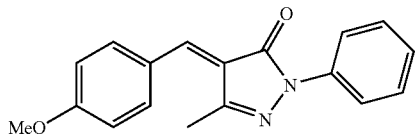

Benzylidene imidazolone such as 5-(4-methoxben-zylidene)-2-phenyl-3,5-dihydroimidazol-4-one:

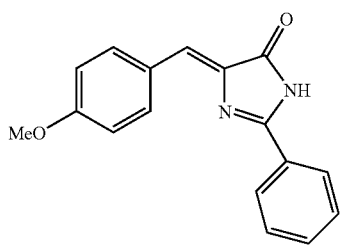

Chalcone such as 1-(2-hydroxy-4-methoxyphenyl)-3-phenylpropenone:

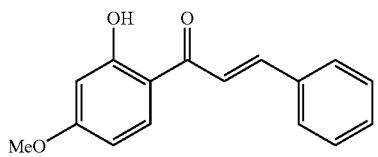

Benzylidene one (screening tautomeric form of the dibenzoylmethanes: L'Oréal FR-2-506,156) such as 3-hydroxy-1-(2-hydroxy-4-methoxyphenyl)-3-phenylpropenone:

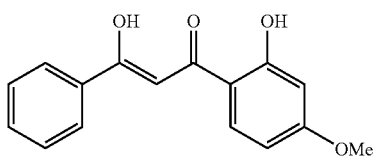

By way of examples of insoluble compounds of formula (XI) in which n=2, for screening out UV radiation, mention may be made of the following families:

Phenylenebis(methylidene-nor-camphor) (Merck EP-O-693,471) such as 1,4-phenylenebis{3-methylidenebicyclo[2.2.1]heptan-2-one}:

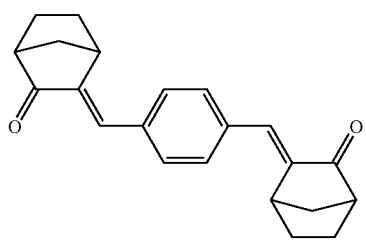

Phenylenebis(methylidenecamphor) (L'Oréal FR-2-528,420) such as 1,4-phenylenebis{3-methylidene-1,7,7-trimethylbicyclo[2.2.1]heptan-2-one}:

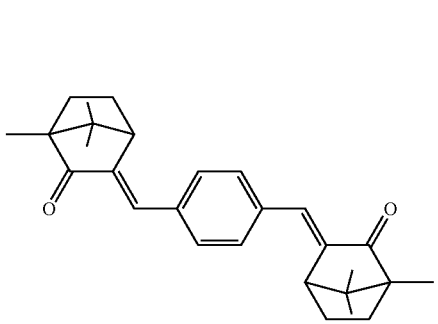

or 1,3-phenylenebis{3-methylidene-1,7,7-trimethylbicyclo[2.2.1]heptan-2-one}:

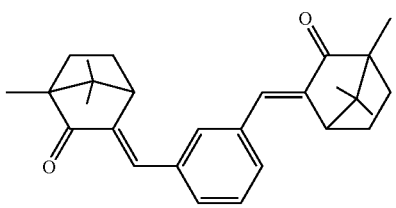

Phenylenebis(methylidenecamphorsulfonamide) (L'Oréal FR-2-529,887) such as ethyl or 2-ethylhexyl 1,4-phenylenebis(3,3'-methylidenecamphor-10, 10'-sulfonamide):

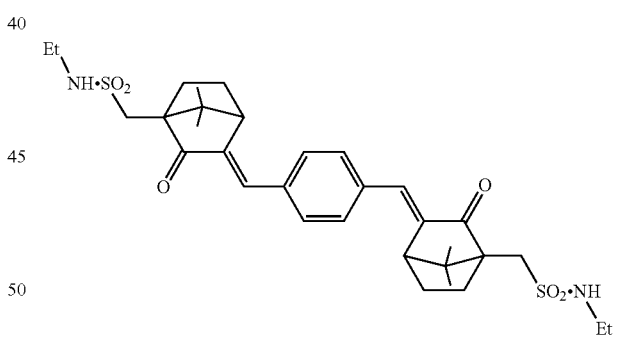

or

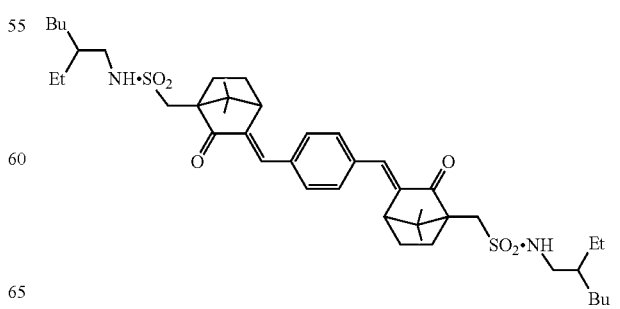

Phenylenebis(methylidenecineole) (E. Mariani et al, 16th IFSCC Congress, New York (1990)) such as 1,4-phenylenebis{5-methylidene-3,3-dimethyl-2-oxabicyclo[2.2.2]octan-6-one}:

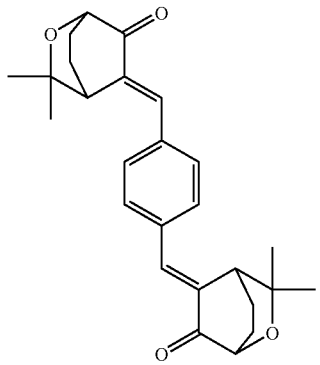

Phenylenebis(methylidene ketotricyclodecane) (Merck EP-O-694,521) such as 1,4-phenylenebis(octahydro-4,7-methano-6-inden-5-one):

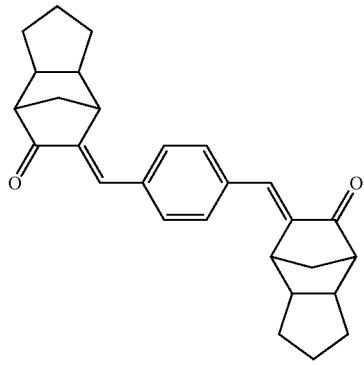

Phenylenebis(alkylene ketone) (Kao JP-04-134,041) such as 1,4-phenylenebis(4,4-dimethylpent-1-en-3-one):

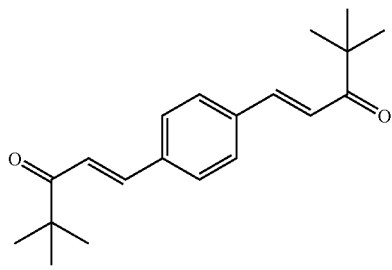

Phenylenebis(methylidenefuranone) (L'Oréal FR-2-638,354) such as 1,4-phenylenebis(4-methylidene-2,2,5,5-tetramethyldihydrofuran-3-one):

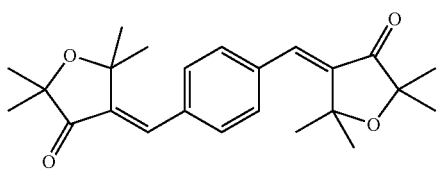

Phenylenebis(methylidene quinuclidinone) (Merck EP-O-714,880) such as 1,4-phenylenebis{2-methylidene-1-azabicyclo[2.2.2]octan-3-one}:

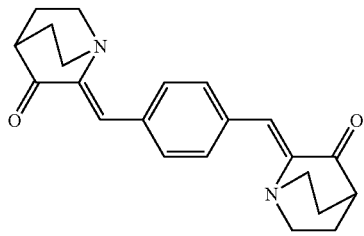

By way of compounds of formula (XII), mention may be made of the following families:
  bis(benzylidene)cycloalkanone such as 2,5-dibenzylidenecyclopentanone:

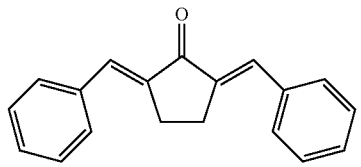

gamma pyrone (Kao JP-04-290,882) such as 2,6-bis(3,4-dimethoxyphenyl)pyran-4-one:

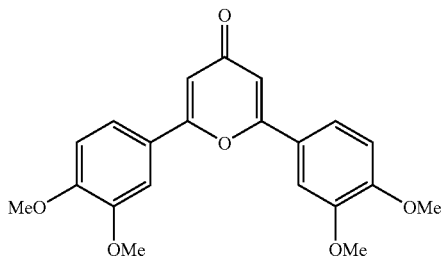

Another family of insoluble screening agents that can be used in the present invention are the acrylonitrile amide, sulfonamide and carbamate derivatives corresponding to the following formula (XIII)

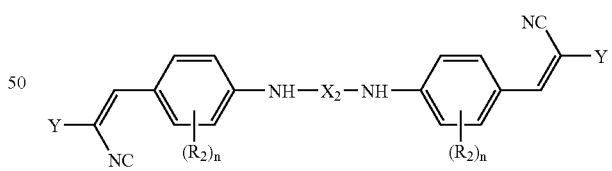

in which:
  $X_2$ represents a divalent radical of formula —(C=O)—$R_{13}$—(C=O)—, —$SO_2$—$R_{13}$-$SO_2$— or —(C=O)—O—$R_{13}$—O—(C=O)—,
  Y represents a radical —(C=O)—$R_4$ or —$SO_2R_5$,
  $R_2$ represents a linear or branched $C_1$-$C_8$ alkyl radical,
  n is 0, 1 or 2,
  $R'_3$ represents a single bond or $R''_3$,
  $R'_3$ represents a linear or branched $C_1$-$C_{30}$ divalent alkylene radical or a linear or branched $C_3$-$C_{30}$ divalent alkenylene radical, which may bear one or more hydroxyl substituents and which may contain, in the carbon-based chain, one or more hetero atoms selected from oxygen, nitrogen and silicon atoms, $R_4$ represents a radical —$OR_6$ or —$NHR_6$, $R_5$ represents a linear or branched $C_1$-$C_{30}$ alkyl radical or a phenyl ring that may be substituted with $C_1$-$C_4$ alkyl or alkoxy radicals, $R_6$ represents a linear or branched $C_1$-$C_{30}$ alkyl or $C_3$-$C_{30}$ alkenyl radical, which may bear one or more hydroxyl substituents and which may contain, in the carbon-based chain, one or more hetero atoms selected from oxygen, nitrogen and silicon atoms.

Although, in formula (XIII) above, only the isomers in which the cyano substituent is in the cis position relative to the para-aminophenyl substituent are represented, this formula must be understood as also encompassing the corresponding trans isomers for each of the two double bonds and, independently, the cyano and para-aminophenyl substituents may be in a cis or trans configuration relative to one another.

Another family of insoluble organic screening agents that may be used according to the present invention is formed by the phenylenebis(benzoxazinone) derivatives of formula:

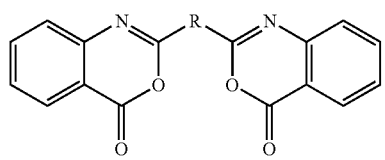

(XIV)

in which R represents a divalent aromatic residue selected from the formulae (e) to (h) below:

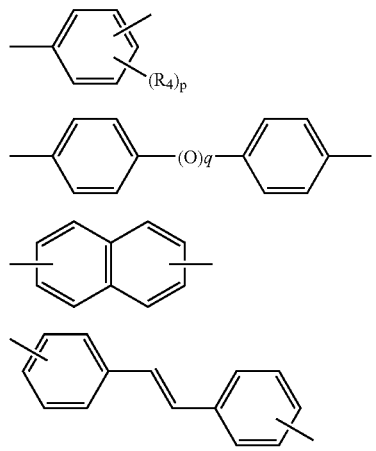

(e)

(f)

(g)

(h)

in which:
each of the symbols $R_4$ independently represents an OH group, a halogen atom, a linear or branched $C_1$-$C_6$ alkyl radical optionally containing a silicon atom, a linear or branched $C_1$-$C_6$ alkoxy radical optionally containing a silicon atom, a linear or branched $C_1$-$C_5$ alkoxycarbonyl radical, or a linear or branched $C_1$-$C_6$ alkylsulfonamide radical optionally containing a silicon atom or an amino acid function, p represents an integer between 0 and 4 inclusive, q represents 0 or 1.

By way of examples of insoluble compounds of formula (XIV) for screening out UV radiation, mention may be made of the following derivatives:

2,2'-p-phenylenebis(3,1-benzoxazin-4-one), commercial product Cyasorb® UV-3638 from the company Cytec, 2,2'-(4,4'-biphenylene)bis(3,1-benzoxazin-4-one), 2,2'-(2,6-naphthylene)bis(3,1-benzoxazin-4-one).

Another particular family of insoluble organic screening agents is polyvalent metal salts (for example, $Ca^{2+}$, $Zn^{2+}$, $Mg^{2+}$, $Ba^{2+}$, $Al^{3+}$ or $Zr^{4+}$) of sulfonated or carboxylated organic screening agents, such as polyvalent metal salts of sulfonated benzylidenecamphor derivatives such as those described in FR-A-2-639,347, polyvalent metal salts of sulfonated benzimidazole derivatives such as those described in EP-A-893,119, and polyvalent metal salts of cinnamic acid derivatives such as those described in JP-87-166,517.

Mention may also be made of complexes of metals or of ammonium or of substituted ammonium of UV-A and/or UV-B organic screening agents such as those described in WO 93/10753, WO 93/11095 and WO 95/05150.

As insoluble organic screening agent, the methylenebis (hydroxyphenylbenzotriazole) derivatives having the following structure will be more particularly selected:

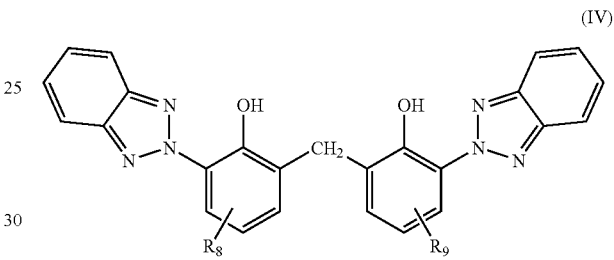

(IV)

in which $R^8$ and $R^9$, which may be identical or different, each represent a $C_1$-$C_{18}$ alkyl radical that may be substituted with one or more radicals selected from $C_1$-$C_4$ alkyl, $C_5$-$C_{12}$ cycloalkyl or aryl, and more particularly compound (a) having the nomenclature 2,2'-methylenebis[6-(2H-benzotriazol-2-yl)-4-(1,1,3,3-tetramethylbutyl)phenol] or methylenebisbenzotriazolyltetramethylbutylphenol marketed in solid form under the name Mixxim BB/100 by Fairmount Chemical and in micronized form under the name Tinosorb M by Ciba Specialty Chemicals.

The insoluble organic screening agents according to the invention are generally in the form of particles having an average size ranging from 10 nm to 5 µm. More particularly, their average size ranges from 10 nm to 2 µm, and in particular from 20 nm to 1.5 µm, and ideally from 30 nm to 1.0 µm.

In general, the average size of the particles will correspond to the number-average diameter distribution.

The average size of the particles can be determined by any conventional method, such as optical methods (quasi-elastic scattering or laser scattering), centrifugation methods or methods comprising visualization under a microscope and image analysis.

The insoluble organic screening agents according to the invention can be placed in the desired particulate form by any ad-hoc means such as, in particular, dry-grinding or grinding in a solvent medium, screening, atomization, micronization or spraying.

The insoluble organic screening agents according to the invention in micronized form can in particular be obtained by a process of grinding an insoluble organic UV-screening agent in the form of particles of coarse size in the presence of a suitable surfactant for improving the dispersion of the particles thus obtained in cosmetic formulations.

An example of a process for micronizing insoluble organic screening agents is described in GB-A-2-303,549 and EP-A-893,119. The grinding apparatus used according to these documents can be a jet mill, a bead mill, a vibration mill or a hammer mill, and preferably a mill with high-speed agitation or an impact mill, and more particularly a rotating-bead mill, a vibrating mill, a tube mill or a shaft mill.

According to this specific process, the surfactants used for grinding said screening agents are alkylpolyglucosides of structure $C_nH_{2n+1}O(C_6H_{10}O_5)_xH$ in which n is an integer from 8 to 16 and x is the average degree of polymerization of the unit $(C_6H_{10}O_5)$ and ranges from 1.4 to 1.6. They can be selected from $C_1$-$C_{12}$ esters of a compound of structure $C_nH_{2n+1}O(C_6H_{10}O_5)_xH$, and more specifically an ester obtained by reacting a $C_1$-$C_{12}$ carboxylic acid such as formic acid, acetic acid, propionic acid, butyric acid, sulfosuccinic acid, citric acid or tartaric acid with one or more free OH functions on the glucoside unit $(C_6H_{10}O_5)$. Said surfactants are generally used at a concentration ranging from 1 to 50% by weight, and more preferably from 5 to 40% by weight, relative to the insoluble screening agent in its micronized form.

Amphiphilic copolymers comprising at least one hydrophilic block and at least one hydrophobic block, such as those described in EP-1-353,642 can also be used to improve the dispersibility of the insoluble organic screening agents in the cosmetic carrier.

The insoluble UV-screening agent(s) of the invention is (are) preferably present at a total concentration of from approximately 0.1 to 25% by weight, and preferably from approximately 0.2 to 20% by weight, relative to the total weight of the composition.

The compositions in accordance with the invention may also comprise other supplementary organic photoprotective agents, that are active in the UV-A and/or UV-B range and that are hydrophilic or lipophilic, in the cosmetic solvents commonly used.

The supplementary organic photoprotective agents are in particular selected from anthranilates; cinnamic derivatives; salicylic derivatives; camphor derivatives; benzophenone derivatives; β,β-diphenylacrylate derivatives; triazine derivatives; benzotriazole derivatives; benzylmalonate derivatives, in particular those mentioned in U.S. Pat. No. 5,624,663; benzimidazole derivatives; imidazolines; bis-benzoazolyl derivatives as described in EP-669,323 and U.S. Pat. No. 2,463,264; p-aminobenzoic acid (PABA) derivatives; benzoxazole derivatives as described in EP-O-832,642, EP-1-027,883, EP-1-300,137 and DE-10162844; screening polymers and screening silicones such as those described in particular in WO 93/04665; dimers derived from a-alkylstyrene, such as those described in DE-19855649; 4,4-diarylbutadienes as described in EP-O-967,200, DE-19746654, DE-1 9755649, EP-A-1-008,586, EP-1-133,980 and EP-133,981, and mixtures thereof.

As examples of supplementary organic photoprotective agents, mention may be made of those denoted below under their INCI name:

Para-Aminobenzoic Acid Derivatives:
PABA,
Ethyl PABA,
Ethyl dihydroxypropyl PABA,
Ethylhexyl dimethyl PABA marketed in particular under the name "Escalol 507" by ISP,
Glyceryl PABA,
PEG-25 PABA marketed under the name "Uvinul P25" by BASF.

Dibenzoylmethane Derivatives:
Butyl methoxydibenzoylmethane marketed in particular under the trademark "Parsol 1789" by Hoffmann Laroche,
Isopropyldibenzoylmethane.

Salicylic Derivatives:
Homosalate marketed under the name "Eusolex HMS" by Rona/EM Industries,
Ethylhexyl salicylate marketed under the name "Neo Heliopan OS" by Haarmann and Reimer,
Dipropylene glycol salicylate marketed under the name "Dipsal" by Scher,
TEA salicylate marketed under the name "Neo Heliopan TS" by Haarmann and Reimer.

Cinnamic Derivatives:
Ethylhexyl methoxycinnamate marketed in particular under the trademark "Parsol MCX" by Hoffmann La Roche,
Isopropyl methoxycinnamate,
Isoamyl methoxycinnamate marketed under the trademark "Neo Heliopan E 1000" by Haarmann and Reimer,
Cinoxate,
DEA methoxycinnamate,
Diisopropyl methylcinnamate,
Glyceryl ethylhexanoate dimethoxycinnamate.

β,β-Diphenylacrylate Derivatives:
Octocrylene marketed in particular under the trademark "Uvinul N539" by BASF,
Etocrylene marketed in particular under the trademark "Uvinul N35" by BASF.

Benzophenone Derivatives:
Benzophenone-1 marketed under the trademark "Uvinul 400" by BASF,
Benzophenone-2 marketed under the trademark "Uvinul D50" by BASF,
Benzophenone-3 or oxybenzone, marketed under the trademark "Uvinul M40" by BASF,
Benzophenone-4 marketed under the trademark "Uvinul MS40" by BASF,
Benzophenone-5,
Benzophenone-6 marketed under the trademark "Helisorb 11" by Norquay,
Benzophenone-8 marketed under the trademark "Spectra-Sorb UV-24" by American Cyanamid,
Benzophenone-9 marketed under the trademark "Uvinul DS-49" by BASF,
Benzophenone-12,
n-Hexyl 2-(4-diethylamino-2-hydroxybenzoyl)benzoate.

Benzylidenecamphor Derivatives:
3-Benzylidenecamphor manufactured under the name "Mexoryl SD" by Chimex,
4-Methylbenzylidenecamphor marketed under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid marketed in particular under the trademark "Eusolex 232" by Merck,
Disodium phenyl dibenzimidazole tetrasulfonate marketed under the trademark "Neo Heliopan AP" by Haarmann and Reimer.

Phenylbenzotriazole Derivatives:
Drometrizole trisiloxane marketed under the name "Silatrizole" by Rhodia Chimie.
Triazine Derivatives:
2,4,6-tris(dineopentyl 4'-aminobenzalmalonate)-s-triazine,
2,4,6-tris(diisobutyl 4'-aminobenzalmalonate)-s-triazine,
Bis-ethylhexyloxyphenol methoxyphenyl triazine marketed under the trademark "Tinosorb S" by Ciba Geigy,
Ethylhexyltriazone marketed in particular under the trademark "Uvinul T150" by BASF,
Diethylhexylbutamidotriazone marketed under the trademark "Uvasorb HEB" by Sigma 3V.
Anthranilic Derivatives:
Menthyl anthranilate marketed under the trademark "Neo Heliopan MA" by Haarmann and Reimer,
Imidazoline Derivatives:
Ethylhexyldimethoxybenzylidenedioxoimidazoline propionate.
Benzalmalonate Derivatives:
Dineopentyl 4'-methoxybenzalmalonate,
Polyorganosiloxane containing benzalmalonate functions, such as Polysilicone-15 marketed under the trademark "Parsol SLX" by Hoffmann La Roche.
4,4-Diarylbutadiene Derivatives:
1,1-Dicarboxy(2,2'-dimethylpropyl)-4,4'-diphenylbutadiene.
Benzoxazole Derivatives:
2,4-bis[5-1 (dimethylpropyl)benzoxazol-2-yl(4-phenyl)imino]-6-(2-ethylhexyl)imino-1,3,5-triazine marketed under the name Uvasorb K2A by Sigma 3V, and mixtures thereof.

The preferred supplementary organic photoprotective agents are selected from among:
Ethylhexyl methoxycinnamate,
Butyl methoxydibenzoylmethane,
Homosalate,
Ethylhexyl salicylate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Terephthalylidenedicamphorsulfonic acid,
Disodium phenyl dibenzimidazole tetrasulfonate,
Ethylhexyltriazone,
Bis-ethylhexyloxyphenol methoxyphenyl triazine,
Diethylhexylbutamidotriazone,
2,4,6-tris(dineopentyl 4-aminobenzalmalonate)-s-triazine,
Drometrizole trisiloxane,
Dineopentyl 4'-methoxybenzalmalonate,
Polysilicone-15,
1,1-dicarboxy(2,2'-dimethylpropyl)-4,4-diphenylbutadiene,
2,4-bis[5-1 (dimethylpropyl)benzoxazol-2-yl(4-phenyl)imino]-6-(2-ethylhexyl)imino-1,3,5-triazine, and mixtures thereof.

The compositions in accordance with the invention may also comprise other inorganic photoprotective agents.

The inorganic photoprotective agents are selected from pigments (average size of the primary particles: generally from 5 nm to 100 nm, preferably from 10 nm to 50 nm) of metal oxides that are coated or uncoated, such as, for example, pigments of titanium oxide (amorphous or crystallized in rutile and/or anatase form), of iron oxide, of zinc oxide, of zirconium oxide or of cerium oxide, or mixtures thereof. Conventional coating agents are, moreover, alumina and/or aluminum stearate. Such coated or uncoated metal oxide pigments are in particular described in EP-518,772 and EP-518,773.

The additional photoprotective agents are generally present in the compositions according to the invention in proportions ranging from 0.01 to 20% by weight relative to the total weight of the composition, and preferably ranging from 0.1 to 10% by weight relative to the total weight of the composition.

The compositions according to the invention may be in any of the forms suitable for topical application, in particular in the form of aqueous gels, or in the form of emulsions obtained by dispersion of a fatty phase (also called oily phase) in an aqueous phase (O/W), or vice versa (W/O), or of multiple emulsions (for example, W/O/W or O/W/O or O/O/W). They can be more or less fluid and can have the appearance of a white or colored cream, of an ointment, of a milk, of a lotion, of a serum, of a paste, of a powder or of a solid stick, and can optionally be packaged in an aerosol and be in the form of a foam or of a spray. These compositions are prepared according to the usual methods.

According to a particular embodiment of the invention, the composition according to the invention is in the form of an emulsion and then comprises at least one oily phase. The proportion of the oily phase of the emulsion can range from 1 to 80% by weight, preferably from 2 to 50% by weight, and better still from 2 to 40% by weight, relative to the total weight of the composition. The fatty substances of the oily phase, in particular the oils, and the emulsifiers and coemulsifiers optionally present, used in the composition in the form of an emulsion, are selected from those conventionally used in cosmetics or dermatology. The emulsifier and the coemulsifier, when they are present, are generally so in a proportion ranging from 0.1 to 30% by weight, preferably from 0.3 to 20% by weight, and better still from 0.5 to 15% by weight, relative to the total weight of the composition.

The emulsion may also contain lipid vesicles in addition to or instead of the emulsifiers and/or coemulsifiers. The emulsions generally contain at least one emulsifier selected from amphoteric, anionic, cationic or nonionic emulsifiers, used alone or as a mixture. The emulsifiers are selected in an appropriate manner according to the continuous phase of the emulsion to be obtained (W/O or O/W). When the emulsion is a multiple emulsion, it generally comprises an emulsifier in the primary emulsion and an emulsifier in the external phase into which the primary emulsion is introduced.

As emulsifiers that can be used for preparing the W/O emulsions, mention may, for example, be made of alkyl esters or ethers of sorbitan, of glycerol or of sugars; silicone surfactants, for instance dimethicone copolyols, such as the mixture of cyclomethicone and of dimethicone copolyol, marketed under the names DC 5225 C and DC 3225 C by Dow Corning, and alkyldimethicone copolyols such as the laurylmethicone copolyol marketed under the name "Dow Corning 5200 Formulation Aid" by Dow Corning, cetyldimethicone copolyol marketed under the name Abil EM 90® by Goldschmidt and the mixture of polyglyceryl-4 isostearate/cetyldimethicone copolyol/hexyl laurate, marketed under the name Abil WE 09® by Goldschmidt. One or more coemulsifiers may also be added thereto, which coemulsifiers may advantageously be selected from the group comprising branched-chain fatty acid esters of polyol, and especially branched-chain fatty acid esters of glycerol and/or of sorbitan, for example polyglyceryl isostearate, such as the product marketed under the name Isolan GI 34 by Goldschmidt, sorbitan isostearate, such as the product marketed under the name Arlacel 987 by ICI, and sorbitan glyceryl isostearate, such as the product marketed under the name Arlacel 986 by ICI, and mixtures thereof.

As emulsifiers that can be used for preparing the O/W emulsions, mention may, for example, be made of nonionic emulsifiers such as oxyalkylenated (more particularly polyoxyethylenated) fatty acid esters of polyols, for example polyethylene glycol stearates, for instance PEG-100 stearate, PEG-50 stearate and PEG-40 stearate; oxyalkylenated fatty acid esters of sorbitan comprising, for example, from 20 to 100 EO, and for example those marketed under the trademarks Tween 20 or Tween 60 by Uniqema; oxyalkylenated (oxyethylenated and/or oxypropylenated) fatty alcohol ethers; alkoxylated or non-alkoxylated sugar esters, for instance sucrose stearate and PEG-20 methylglucose sesquistearate; sorbitan esters such as the sorbitan palmitate marketed under the name Span 40 by Uniqema; esters of diacid and of fatty alcohol, such as dimyristyl tartrate; mixtures of these emulsifiers, for instance the mixture of glyceryl stearate and of PEG-100 stearate (CTFA name: glycerylstearate/PEG-100 stearate) marketed under the name Arlacel 165 by Uniqema and under the name Simulsol 165 by Seppic; or the mixture of dimyristyl tartrate, of cetearyl alcohol, of Pareth-7 and of PEG-25 laureth-25, marketed under the name Cosmacol PSE by Sasol (CTFA name: dimyristyl tartrate/cetearyl alcohol/12-15 Pareth 7/PPG 25 laureth 25).

Coemulsifiers may be added to these emulsifiers, for instance fatty alcohols containing from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol or oleyl alcohol, or fatty acids.

Emulsions free of emulsifying surfactants or containing less than 0.5% thereof relative to the total weight of the composition may also be prepared, by using suitable compounds for stabilizing said emulsions, for example amphiphilic polymers, fillers, thickeners or gelling agents.

When the composition of the invention is in emulsion form, it comprises at least one oily phase that contains at least one oil, in particular a cosmetic oil. The term "oil" means a fatty substance that is liquid at room temperature (25° C.).

As oils that can be incorporated in the compositions of the invention, use may, for example, be made of hydrocarbon-based oils of animal origin, such as perhydrosqualene (or squalane); hydrocarbon-based oils of plant origin, such as caprylic/capric acid triglycerides, for instance those marketed by Stearineries Dubois or those marketed under the names Miglyol 810, 812 and 818 by Dynamit Nobel, or alternatively oils of plant origin, for example sunflower oil, corn oil, soybean oil, marrow oil, grapeseed oil, sesame oil, hazelnut oil, apricot oil, macadamia oil, arara oil, coriander oil, castor oil, avocado oil, jojoba oil or shea butter oil; synthetic oils; silicone oils, for instance volatile or non-volatile polymethylsiloxanes (PDMS) containing a linear or cyclic silicone chain, which are liquid or pasty at ambient temperature; fluoro oils, such as partially hydrocarbon-based and/or partially silicone-based fluoro oils, for instance those described in document JP-A-2-295912; ethers such as dicaprylyl ether (CTFA name: dicaprylyl ether); and $C_{12}$-$C_{15}$ fatty alcohol benzoates (Finsolv TN from Finetex); arylalkyl benzoate derivatives such as 2-phenylethyl benzoate (X-Tend 226 from ISP); amidated oils such as isopropyl N-lauroylsarcosinate (Eldew SL-205 from Ajimoto), and mixtures thereof.

The oily phase may also comprise one or more fatty substances selected, for example, from fatty alcohols (cetyl alcohol, stearyl alcohol, cetearyl alcohol), fatty acids (stearic acid) or waxes (paraffin, polyethylene wax, carnauba wax, beeswax).

The compositions of the invention may contain one or more organic solvents which may be selected from the group consisting of hydrophilic organic solvents, lipophilic organic solvents, amphiphilic solvents, or mixtures thereof.

Among the hydrophilic organic solvents, mention may, for example, be made of linear or branched monohydric alcohols containing from 1 to 8 carbon atoms, such as ethanol, propanol, butanol, isopropanol or isobutanol; polyethylene glycols containing from 6 to 80 ethylene oxides; polyols such as propylene glycol, isoprene glycol, butylene glycol, glycerol or sorbitol; monoalkyl or dialkyl isosorbide in which the alkyl groups contain from 1 to 5 carbon atoms, such as dimethyl isosorbide; glycol ethers, such as diethylene glycol monomethyl ether or diethylene glycol monoethyl ether, and propylene glycol ethers such as dipropylene glycol methyl ether.

As amphiphilic organic solvents, mention may be made of polypropylene glycol (PPG) derivatives, such as esters of polypropylene glycol and of a fatty acid, or of PPG and of a fatty alcohol, for instance PPG-23 oleyl ether and PPG-36 oleate. As lipophilic organic solvents, mention may, for example, be made of fatty esters such as diisopropyl adipate, dioctyl adipate or alkyl benzoates.

The compositions in accordance with the present invention may also comprise conventional cosmetic adjuvants selected from softeners, humectants, opacifiers, stabilizers, emollients, silicones, anti-foams, fragrances, preservatives, anionic, cationic, nonionic, zwitterionic or amphoteric surfactants, fillers, polymers, propellants, basifying or acidifying agents, or any other ingredient normally used in cosmetics and/or dermatology.

As hydrophilic thickeners, mention may be made of carboxyvinyl polymers such as carbopols (carbomers) and Pemulen (acrylate/$C_{10}$-$C_{30}$ alkyl acrylate copolymer); cellulose derivatives such as hydroxyethylcellulose; polysaccharides, and in particular gums such as xanthan gum; and mixtures thereof.

As lipophilic thickeners, mention may be made of modified clays such as hectorite and derivatives thereof, for instance the products marketed under the name Bentone.

As preservatives, mention may be made of para-hydroxybenzoic acid esters, also called Parabens® (in particular methyl paraben, ethyl paraben, propyl paraben), phenoxyethanol, compounds which release formaldehyde, such as, for example, imidazolidinylurea or diazolidinylurea, chlorhexidine digluconate, sodium benzoate, caprylyl glycol, iodopropynyl butyl carbamate, pentylene glycol, alkyltrimethylammonium bromide, such as myristyltrimethylammonium bromide (CTFA name: myrtrimonium bromide), dodecyltrimethylammonium bromide, hexadecyltrimethylammonium bromide, and mixtures thereof, such as the mixture marketed under the name Cetrimide® by FEF Chemicals. The preserving agent may be present in the composition according to the invention at a content ranging from 0.001 to 10% by weight, relative to the total weight of the composition, especially ranging from 0.1 to 5% by weight, and in particular ranging from 0.2 to 3% by weight.

As fillers that may be incorporated in the compositions of the invention, mention may, for example, be made of pigments; silica powder; talc; polyamide particles, and in particular those marketed under the name Orgasol by Atochem; polyethylene powders; powders of natural organic materials such as starch powders, in particular powders of crosslinked or non-crosslinked cornstarch, wheat starch or rice starch, such as the starch powders crosslinked with octenylsuccinate anhydride marketed under the name Dry-Flo by National Starch; microspheres based on acrylic copolymers, such as those made of ethylene glycol dimethacrylate/lauryl methacrylate copolymer marketed by Dow Corning under the name Polytrap; polymethyl methacrylate powders such as those marketed under the name Micropearl M 100 by Matsumoto; expanded powders such as hollow microspheres, and in particular the microspheres marketed under the name Expancel by Kemanord Plast or under the name Micropearl F 80 ED by Matsumoto; silicone resin microbeads such as those marketed under the name Tospearl by Toshiba Silicone; polyurethane powders such as the hexamethylene diisocyanate/trimethylol hexyl lactone copolymer powder marketed under the name Plastic Powder D-400 by Toshiba Pigment (CTFA name: HDI/trimethylol hexyllactone crosspolymer); and mixtures thereof. When they are present, these fillers may be in amounts ranging from 0.001 to 20% by weight, preferably from 0.1 to 10% by weight, and better still from 1 to 5% by weight, relative to the total weight of the composition.

Of course, one skilled in this art will take care to choose the possible supplementary compound(s) mentioned above and/or the amounts thereof in such a way that the advantageous properties intrinsically associated with the combination in accordance with the invention are not, or are not substantially, impaired by the envisaged addition(s).

The compositions according to the invention are generally suitable for topical application to the skin and therefore generally comprise a physiologically acceptable medium, i.e., a medium compatible with the skin and/or its integuments. It is preferably a cosmetically acceptable medium, i.e., a medium that has a pleasant color, odor and feel and that does not generate any unacceptable discomfort (stinging, tautness, redness) that may dissuade the consumer from using this composition.

The compositions according to the invention may constitute a skincare product, in particular for the face, the neck, the area around the eyes or the body; alternatively a skin makeup product such as a complexion product (especially a foundation), an eyeshadow, a blusher, an eyeliner, a concealer product, a body makeup product, an anti-sun product or else a skin cleansing product. Preferably, the composition according to the invention will be an anti-sun product.

The composition is generally not rinsed off, but it may be rinsed off if it constitutes a cleansing product, in particular a foaming product.

The present invention also features a cosmetic regime or regimen for treating a keratin material such as the skin, the eyelashes, the eyebrows, the nails or the mucous membranes, characterized in that a composition as defined above is applied to the keratin material.

According to another aspect, the invention also relates to a cosmetic assembly comprising:
i) a container delimiting at least one compartment, said container being closed by means of a closing member; and
ii) a composition as described above and placed inside said compartment.

The container may be in any appropriate form. It may in particular be in the form of a bottle, a tube, a jar, a case, a box, a sachet or a carton.

The closing member may be in the form of a removable stopper, a lid, a cap, a tear-off strip or a capsule, in particular of the type comprising a body attached to the container and a cover cap articulated on the body. It may also be in the form of a member for selectively closing the container, in particular a pump, a valve or a flap valve.

The product may be contained directly in the container, or indirectly. By way of example, the product may be arranged on an impregnated carrier, in particular in the form of a wipe or of a pad, and arranged (individually or in plurality) in a box or in a sachet. Such a carrier incorporating the product is described, for example, in WO 01/03538.

The closing member may be coupled to the container by screwing. Alternatively, the coupling between the closing member and the container is done other than by screwing, in particular via a bayonet mechanism, by click-fastening, gripping, welding, bonding or by magnetic attraction. The term "click-fastening" is in particular intended to mean any system involving the crossing of a bead or cord of material by elastic deformation of a portion, in particular of the closing member, followed by return to the elastically unconstrained position of said portion after the crossing of the bead or cord.

The container may be at least partially made of thermoplastic material. By way of examples of thermoplastic materials, mention may be made of polypropylene or polyethylene.

Alternatively, the container is made of non-thermoplastic material, in particular of glass or of metal (or alloy).

The container may have rigid walls or deformable walls, in particular in the form of a tube or of a tubular bottle.

The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container.

The compositions according to the invention may be in the form of sprayable fluid lotions in accordance with the invention that are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps that use compressed air as propellant. The latter are described in U.S. Pat. Nos. 4,077,441 and 4,850,517.

The compositions packaged as an aerosol in accordance with the invention generally contain conventional propellants such as, for example, hydrofluoro compounds, dichlorodifluoromethane, difluoroethane, dimethyl ether, isobutane, n-butane, propane or trichlorofluoromethane. They are preferably present in amounts ranging from 15 to 50% by weight relative to the total weight of the composition.

In order to further illustrate the present invention and the advantages thereof, the following specific examples are given, it being understood that same are intended only as illustrative and in nowise limitative. In said examples to follow, all parts and percentages are given by weight, unless otherwise indicated.

The following anti-sun/sunscreen formulations were prepared; the amounts are indicated as percentages by weight:

| Compositions | Ex 1 | Ex 2 | Ex 3 | Ex 4 | Ex 5 |
|---|---|---|---|---|---|
| PHASE A: | | | | | |
| Polydimethylsiloxane | 0.5 | 0.5 | 0.5 | 0.5 | 0.5 |
| Preservatives | 1.0 | 1.0 | 1.0 | 1.0 | 1.0 |
| Stearic acid | 1.5 | 1.5 | 1.5 | 1.5 | 1.5 |
| Mixture of glyceryl monostearate/PEG (100 EO) stearate | 1.0 | 1.0 | 1.0 | 1.0 | 1.0 |
| Mixture of cetylstearyl glucoside/cetylstearyl alcohol | 2.0 | 2.0 | 2.0 | 2.0 | 2.0 |
| $C_{12}/C_{15}$ alcoholbenzoate | 5.0 | — | 5.0 | 5.0 | — |
| Isohexadecane | 1.0 | 1.0 | 1.0 | 1.0 | 1.0 |

-continued

| Compositions | Ex 1 | Ex 2 | Ex 3 | Ex 4 | Ex 5 |
|---|---|---|---|---|---|
| Cetyl alcohol | 0.5 | 0.5 | 0.5 | 0.5 | 0.5 |
| Butyl methoxydibenzoyl-methane | 2.0 | 2.5 | 2.0 | 2.0 | 2.0 |
| Octocrylene | 9.0 | 10.0 | 9.0 | 10.0 | 10.0 |
| Drometrizole trisiloxane | 1.0 | — | 4.0 | — | — |
| Methylenebisbenzotriazolyl-tetramethylbutylphenol | 1.0 | 3.0 | 1.0 | 3.0 | 3.0 |
| $TiO_2$ | 3.0 | 5.0 | — | 5.0 | 5.0 |
| PHASE B: | | | | | |
| N-(2-hydroxyethyl)urea | 5.0 | 10.0 | 5.0 | 5.0 | 10.0 |
| Deionized water | qs 100 | qs 100 | qs 100 | qs 100 | qs 100 |
| Sequestering agent | 0.1 | 0.1 | 0.1 | 0.1 | 0.1 |
| Glycerol | 5.0 | 5.0 | 5.0 | 5.0 | 5.0 |
| Xanthan gum | 0.2 | 0.2 | 0.2 | 0.2 | 0.2 |
| Monocetyl phosphate | 1.0 | 1.0 | 1.0 | 1.0 | 1.0 |
| PHASE C: | | | | | |
| Acrylic acid/stearyl methacrylate copolymer | 0.2 | 0.2 | 0.2 | 0.2 | 0.2 |
| Triethanolamine | qs | qs | qs | qs | qs |

Procedure:

The aqueous phase (phase B) containing all of its ingredients is heated to 80° C. in a water bath. The fatty phase (phase A) containing all of its ingredients is heated to 80° C. in a water bath. A is emulsified in B with stirring of rotor-stator type (device from the company Moritz). Phase C is incorporated and the mixture is allowed to return to ambient temperature with moderate stirring. The triethanolamine is introduced so as to adjust the pH to the desired value at the end of manufacture.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic composition comprising at least one system for screening out UV radiation, and further comprising:

(a) at least one insoluble organic UV-screening agent, and (b) at least one hydroxyalkylurea compound of formula (1):

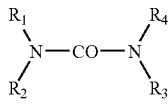

(1)

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate, or isomer thereof, formulated into (c) a topically applicable, cosmetically acceptable carrier therefor.

2. The cosmetic composition as defined by claim 1, wherein, in formula 1, $R_1$ is a hydroxyalkyl group and $R_2$, $R_3$ and $R_4$ represent, independently of one another, a hydrogen atom or a $C_1$-$C_4$ alkyl radical.

3. The cosmetic composition as defined by claim 2, wherein, in formula 1, $R_1$ is a hydroxyalkyl group and $R_2$, $R_3$ and $R_4$ each represent a hydrogen atom.

4. The cosmetic composition as defined by claim 1, said at least one compound of formula 1 being selected from the group consisting of N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-ropyl)urea; N-(trishydroxymethylmethyl)urea; N-ethyl-N'-(2-hydroxyethyl)urea; N,N-bis-(2-hydroxyethyl)urea; N,N'-bis-(2-hydroxyethyl)urea; N,N-bis-(2-hydroxypropyl)urea; N,N'-bis-(2-hydroxypropyl)urea; N,N-bis-(2-hydroxyethyl)-N'-propylurea; N,N-bis-(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis-(2-hydroxyethyl)-N',N'-dimethylurea; N,N,N',N'-tetrakis-(2-hydroxyethyl)urea; and N',N'-bis-(2-hydroxyethyl)-N',N'-bis-(2-hydroxypropyl)urea; and mixtures thereof.

5. The cosmetic composition as defined by claim 1, wherein said at least one compound of formula 1 is N-(2-hydroxyethyl)urea.

6. The cosmetic composition as defined by claim 1, comprising from 0.01 to 50% by weight of said at least one compound of formula 1.

7. The cosmetic composition as defined by claim 1, said at least one insoluble organic UV-screening agent being selected from the group consisting of oxalanilide, triazine, benzotriazole, vinylamide, cinnamide, benzazole, benzofuran, arylvinylidene ketone, acrylonitrile amide, acrylonitrile sulfonamide, acrylonitrile carbamate and phenylenebisbenzoxazinone compounds, and mixtures thereof.

8. The cosmetic composition as defined by claim 1, said at least one insoluble organic UV-screening agent being selected from the group consisting of polyvalent metal salts of sulfonated or carboxylated organic screening agents.

9. The cosmetic composition as defined by claim 8, said at least one insoluble UV-screening agent being selected from the group consisting of polyvalent metal salts of sulfonated benzylidenecamphor derivatives, polyvalent metal salts of sulfonated benzimidazole derivatives, and polyvalent metal salts of cinnamic acid derivatives.

10. The cosmetic composition as defined by claim 1, said at least one insoluble organic UV-screening agent comprising a methylenebis(hydroxyphenylbenzotriazole) derivative having the structure below:

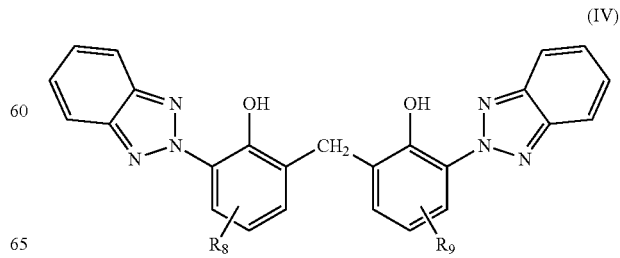

(IV)

in which $R_8$ and $R_9$, which may be identical or different, each represent a $C_1$-$C_{18}$ alkyl radical that may be substituted with one or more $C_1$-$C_4$ alkyl, $C_5$-$C_{12}$ cycloalkyl or aryl radicals.

11. The cosmetic composition as defined by claim 10, wherein said at least one insoluble organic UV-screening agent comprises 2,2'-methylenebis[6-(2H-benzotriazol-2-yl)-4-(1,1,3,3-tetramethylbutyl)phenol].

12. The cosmetic composition as defined by claim 1, said at least one insoluble organic UV-screening agent being in the form of particles having an average size ranging from 10 nm to 5 μm.

13. The cosmetic composition as defined by claim 12, in which the average particle size ranges from 10 nm to 2 μm.

14. The cosmetic composition as defined by claim 1, said at least one insoluble organic UV-screening agent being obtained by grinding same in the form of particles of coarse size in the presence of a surfactant.

15. The cosmetic composition as defined by claim 1, said surfactant comprising an alkylpolyglucoside of structure $C_nH_{2n+1}O(C_6H_{10}O_5)_xH$ in which n is an integer ranging from 8 to 16 and x is the average degree of polymerization of the unit ($C_6H_{10}O_5$) and ranges from 1.4 to 1.6.

16. The cosmetic composition as defined by claim 15, said surfactant being employed at a concentration ranging from 1 to 50% by weight relative to the insoluble screening agent.

17. The cosmetic composition as defined by claim 1, further comprising at least one amphiphilic copolymer having at least one hydrophilic block and at least one hydrophobic block.

18. The cosmetic composition as defined by claim 1, said at least one insoluble UV-screening agent being present in an amount of from about 0.1 to 25% by weight thereof.

19. The cosmetic composition as defined by claim 1, formulated as a skincare product, a skin makeup product, an antisun/sunscreen product or a skin cleansing product.

20. The cosmetic composition as defined by claim 1, formulated as an antisun/sunscreen product.

21. A regime or regimen for photoprotecting a keratin material against the damaging effects of UV radiation, comprising topically applying thereon a cosmetic composition comprising at least one system for screening out UV radiation, and further comprising:
(a) at least one insoluble organic UV-screening agent, and
(b) at least one hydroxyalkylurea compound of formula 1:

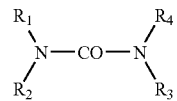

(1)

in which $R_1$, $R_2$, $R_3$ and $R_4$ each independently represent a hydrogen atom, a $C_1$-$C_4$ alkyl radical or a $C_2$-$C_6$ hydroxyalkyl radical containing from 1 to 5 hydroxyl groups, at least one of the radicals $R_1$-$R_4$ representing a hydroxyalkyl group, or salt, solvate or isomer thereof, formulated into (c) a topically applicable, cosmetically acceptable carrier therefor.

22. The regime or regimen as defined by claim 21, said keratin material comprising human skin, hair, eyelashes, eyebrows, nails and/or mucous membranes.

23. The regime or regimen as defined in claim 14, for improving the comfort, after application of said at least one system for screening out UV radiation.

24. A cosmetic assembly comprising:
(i) a container delimiting at least one compartment, said container being closed by means of a closing member; and
(ii) a composition as defined by claim 1 and placed inside said compartment.

* * * * *